US012788409B2

(12) United States Patent
Branthover et al.

(10) Patent No.: US 12,788,409 B2
(45) Date of Patent: Nov. 10, 2026

(54) SURGICAL TOOLS AND METHODS OF USE

(71) Applicant: WRIGHT MEDICAL TECHNOLOGY, INC., Memphis, TN (US)

(72) Inventors: Lewis Pearce Branthover, Memphis, TN (US); George Matthew Awtrey, Bartlett, TN (US); Zachary Korman, St. Louis, MO (US); Robert Michael Carlo, III, Lakeland, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 0 days.

(21) Appl. No.: 19/322,912

(22) Filed: Sep. 9, 2025

(65) Prior Publication Data

US 2026/0000413 A1 Jan. 1, 2026

Related U.S. Application Data

(62) Division of application No. 18/638,985, filed on Apr. 18, 2024, now Pat. No. 12,433,606, which is a division of application No. 17/421,146, filed as application No. PCT/US2020/019138 on Feb. 21, 2020, now Pat. No. 12,042,156.

(60) Provisional application No. 62/846,943, filed on May 13, 2019.

(51) Int. Cl.
*A61B 17/15* (2006.01)
*A61B 17/56* (2006.01)

(52) U.S. Cl.
CPC ...... *A61B 17/151* (2013.01); *A61B 2017/565* (2013.01)

(58) Field of Classification Search
CPC . A61B 17/151; A61B 17/848; A61B 17/1775; A61B 2017/565
See application file for complete search history.

(56) References Cited

U.S. PATENT DOCUMENTS

| | | | | |
|---|---|---|---|---|
| 5,843,085 A * | 12/1998 | Graser | A61B 17/151 | 606/87 |
| 9,044,250 B2 * | 6/2015 | Olsen | A61B 17/151 | |
| 9,060,790 B2 * | 6/2015 | Wayne | A61B 17/1775 | |
| 2014/0094861 A1 * | 4/2014 | Fallin | A61B 17/8897 | 606/86 R |
| 2016/0213384 A1 * | 7/2016 | Fallin | A61B 17/151 | |
| 2017/0014173 A1 * | 1/2017 | Smith | A61B 17/8866 | |
| 2018/0250024 A1 * | 9/2018 | Woodard | A61B 17/1775 | |

* cited by examiner

*Primary Examiner* — Tracy L Kamikawa
(74) *Attorney, Agent, or Firm* — DUANE MORRIS LLP

(57) ABSTRACT

A cut guide includes a first face and an opposed second face. The cut guide further includes a first aperture and a second aperture extending through the cut guide from the first face to the second face. The first and second apertures are configured to guide a surgical tool in cutting a bone. The cut guide further includes a first hole extending through the cut guide from the first face to the second face. The cut guide further includes a second hole extending through the cut guide. A central axis of the second hole is oriented at an acute angle to the second face. The first and second holes are configured to receive a wire to position the guide against the bone.

19 Claims, 21 Drawing Sheets

SURGICAL TOOLS AND METHODS OF USE

CROSS-REFERENCE TO RELATED APPLICATION

This application is a divisional application of U.S. patent application Ser. No. 17/421,146, filed Jul. 7, 2021, which is a national stage application, filed under 35 U.S.C. 371, of International Patent Application No. PCT/US2020/019138, filed on Feb. 21, 2020, which claims priority to U.S. Provisional Patent Application No. 62/846,943, filed on May 13, 2019, the entireties of which are incorporated herein by reference.

BACKGROUND

Hallux valgus deformity is a common forefoot deformity. Such a deformity can lead to painful bunions, transfer metatarsalgia, and hammer or claw toes. Various methods are used to correct hallux valgus deformity. One such method is to perform a chevron osteotomy of the first metatarsal to separate the first metatarsal into distal and proximal portions. The distal and proximal portions are then positioned as desired and secured in position using bone screws, plates or other fixation means.

SUMMARY

In one aspect, a cut guide is disclosed that includes a first face and an opposed second face. The cut guide further includes a first aperture and a second aperture extending through the cut guide from the first face to the second face. The first and second apertures are configured to guide a surgical tool in cutting a bone. The cut guide further includes a first hole extending through the cut guide from the first face to the second face. The cut guide further includes a second hole extending through the cut guide. A central axis of the second hole is oriented at an acute angle to the second face. The first and second holes are configured to receive a wire to position the guide against the bone.

In another aspect, a targeting guide is disclosed that has a coupling member, an arm extending from the coupling member, and a targeting member coupled to the arm. The coupling member includes a coupling hole extending through the coupling member. The coupling hole is configured to receive a wire. The coupling member further includes a first projection extending from a bone facing surface of the coupling member. The first projection is configured to engage a bone. The targeting member includes at least one targeting hole for receiving and aligning a wire inserted into the bone.

In another aspect, a kit is disclosed that has a cut guide and a targeting guide. The cut guide includes a first face and an opposed second face. The cut guide further includes a first aperture and a second aperture extending through the cut guide from the first face to the second face, wherein the first and second apertures are configured to guide a surgical tool in cutting a bone. The targeting guide includes a coupling member, an arm extending from the coupling member, and a targeting member coupled to the arm. The coupling member includes a coupling hole extending through the coupling member, wherein the coupling hole is configured to receive a coupling wire inserted in the bone. The coupling member further includes a first projection extending from a bone facing surface of the coupling member, wherein the first projection is configured to engage the bone. The targeting member includes at least one targeting hole for receiving and aligning a targeting wire inserted in the bone.

In another aspect, a method is disclosed. The method includes inserting a first wire into a bone. The method further includes sliding a cut guide over the first wire such that the first wire is disposed within a first hole of the cut guide. The method further includes inserting a second wire through a second hole of the cut guide such that the first wire and the second wire define an acute angle. The method further includes separating the bone into a first bone portion and a second bone portion using a surgical tool by inserting the surgical tool through at least one aperture in the cut guide.

In another aspect, a method is disclosed. The method includes inserting a wire into a bone. The method further includes sliding the wire through a hole of a targeting guide. The method further includes engaging a projection extending from a bone facing surface of the targeting guide with the bone. The method further includes inserting a first targeting wire through a first targeting hole of the targeting guide. The method further includes inserting a second targeting wire through a second targeting hole of the targeting guide, wherein the first and second targeting holes are equally spaced from the bone facing surface. The method further includes inserting a first screw into the bone along a trajectory defined by the first targeting wire. The method further includes inserting a second screw into the bone along a trajectory defined by the second targeting wire.

BRIEF DESCRIPTION OF THE DRAWINGS

The features of the embodiments described herein will be more fully disclosed in the following detailed description, which is to be considered together with the accompanying drawings wherein like numbers refer to like parts.

DETAILED DESCRIPTION

Figure 1:
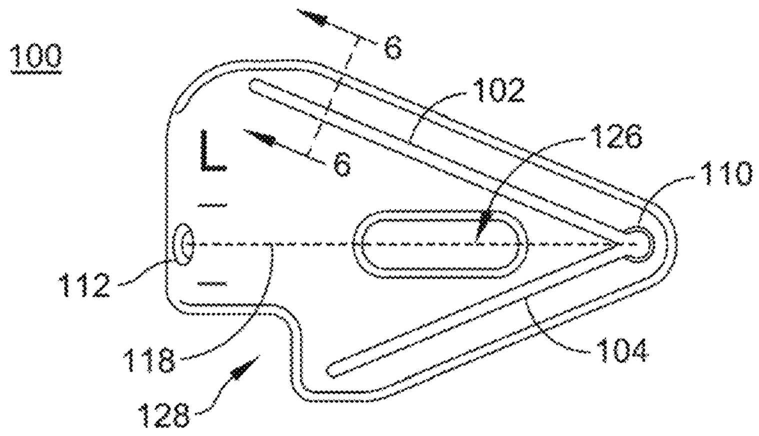
FIGS. 1-4 are top, side, bottom, and end views, respectively, of a cut guide, according to one embodiment described herein.
Figure 2:
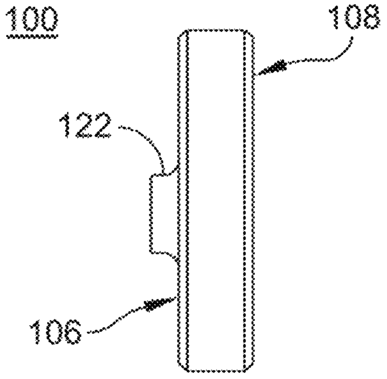

This description of the exemplary embodiments is intended to be read in connection with the accompanying drawings, which are to be considered part of the entire written description. The drawing figures are not necessarily to scale and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

This disclosure describes cutting guides and targeting guides and methods of their use. The cutting guides and targeting guides described herein are particularly well suited for use in procedures to correct pronounced hallux valgus angles of the first toe. However, they may be used in any appropriate procedure.

FIGS. 1-7 show a cut guide 100 according to one embodiment. FIG. 1 shows a top view of cut guide 100. Cut guide 100 includes a first aperture 102 and a second aperture 104 extending between a first face 106 and a second face 108 of cut guide 100 (shown in FIG. 2) configured to guide a cutting instrument (e.g., a surgical saw) in cutting a bone. In one embodiment, first 102 and second 104 apertures are oriented at an angle with respect to one another such that the cutting instrument can form a chevron-shaped cut in a bone, as will be described herein. For example, in some embodiments, first 102 and second 104 apertures are oriented at an angle of about 45 degrees with respect to one another. In some embodiments, first 102 and second 104 apertures meet at an intersection. First 102 and second 104 apertures may be the same length or, as shown in FIG. 1, may be different lengths. Cut guide 100 may be provided in both a left and right configuration for use on the left and right foot, respectively.

Figure 7:
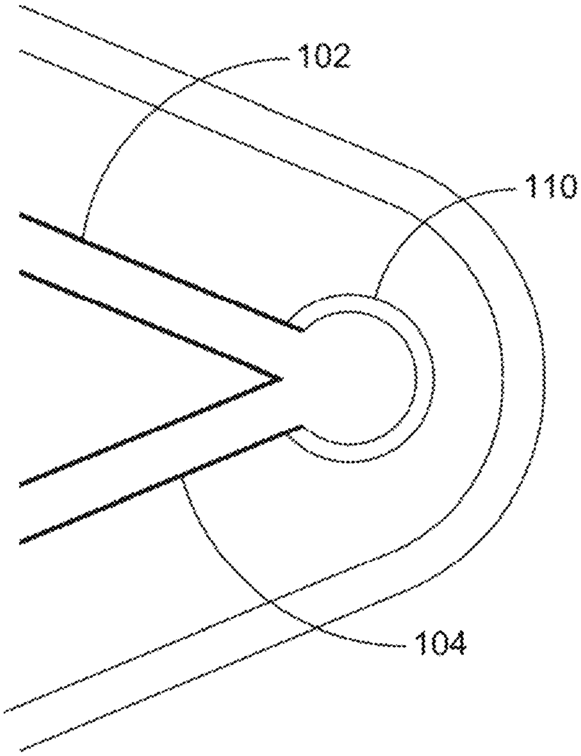
FIG. 7 is a detail view of a first hole of the cut guide of FIG. 1.
Figure 8:
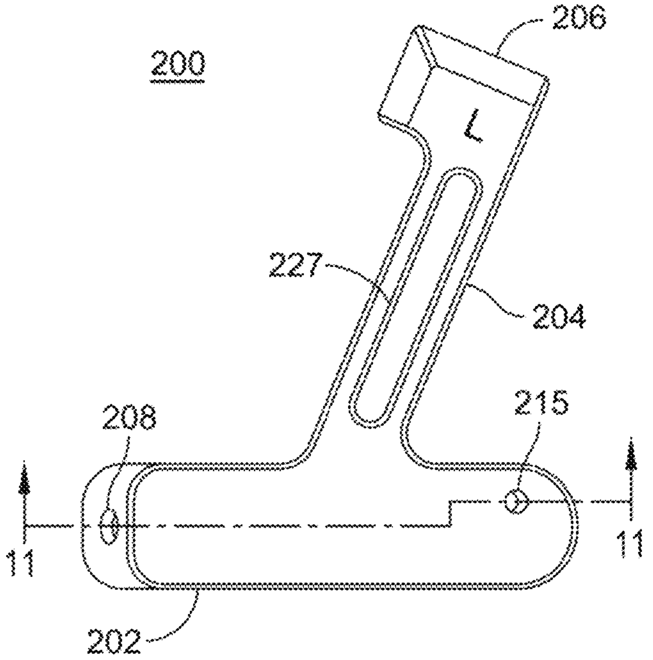
FIGS. 8-10 are front, side, and rear views, respectively, of a targeting guide according to one embodiment described herein.

In some embodiments, cut guide 100 further includes a first hole 110 extending between first face 106 and second face 108 and configured to receive a k-wire, Steinmann pin, or other appropriate wire or pin (hereinafter, k-wires, Steinmann pins, and other wires or pins are collectively referred to as a "wire") inserted into a bone of a patient, as described herein. FIG. 7 shows the first hole 110 in detail. In some embodiments, first hole 110 is positioned at the intersection of first and second apertures 102, 104. Further, in some embodiments, the central axis 111 (shown in FIG. 5) of first hole 110 is perpendicular to first face 106 and/or second face 108.

Figure 3:
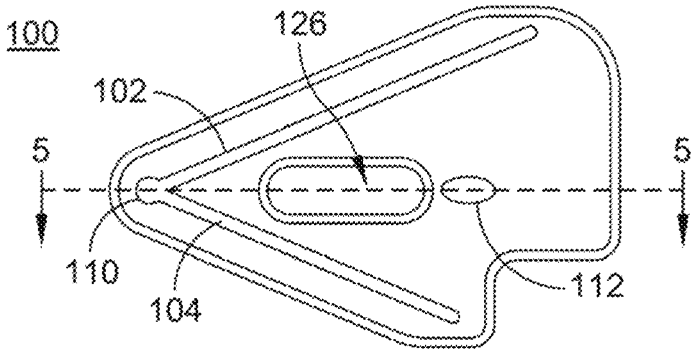
Figure 4:
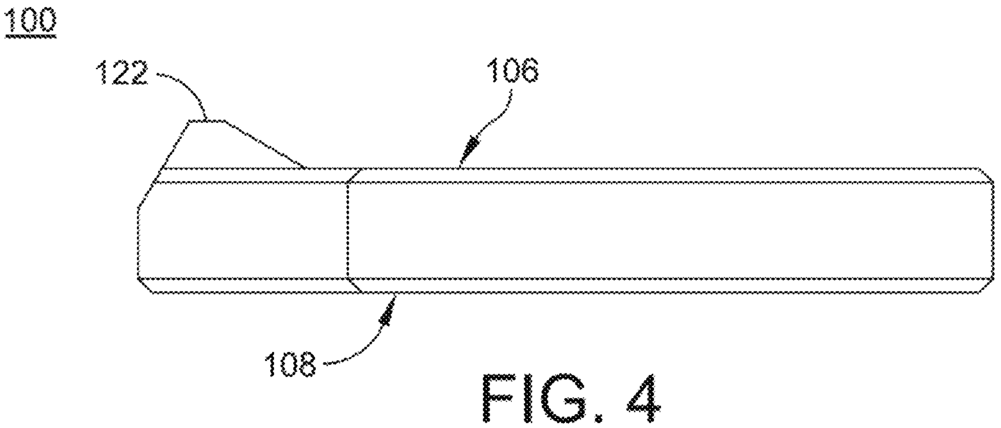
Figure 5:
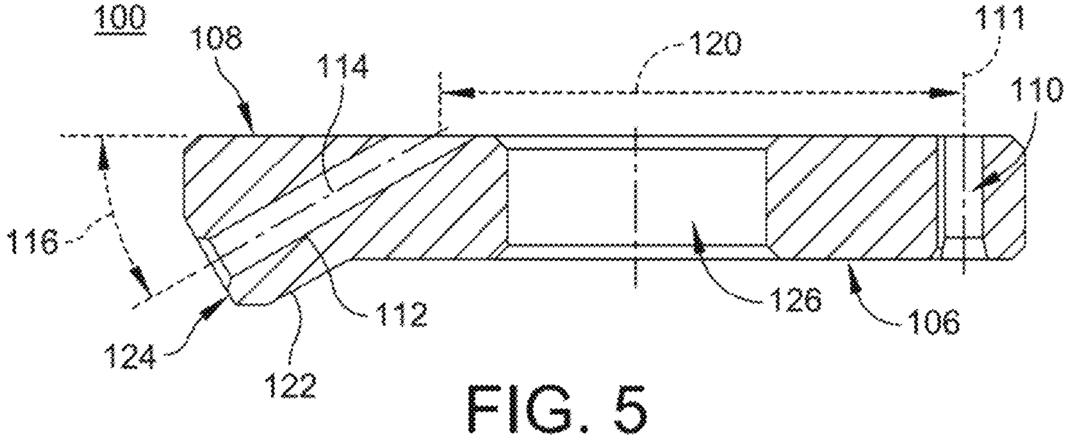
FIG. 5 is a cross-sectional view of the cut guide of FIG. 1.
Figure 6:
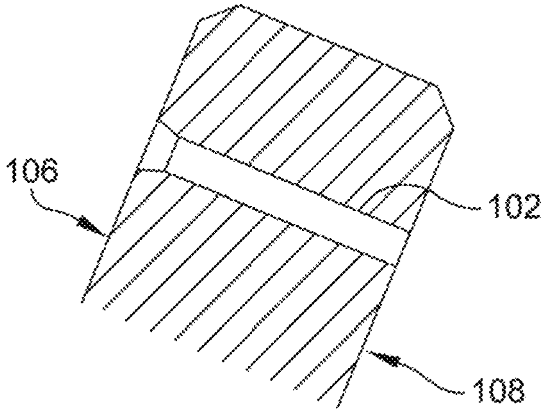
FIG. 6 is a detail cross-sectional view showing an aperture of the cut guide of FIG. 1.

As shown in the top view of FIG. 1 and the bottom view of FIG. 3, cut guide 100 also includes a second hole 112 configured to receive a wire inserted into a bone of a patient, as described herein. As shown in FIG. 5, in at least some embodiments, second hole 112 defines a central axis 114 that forms an acute angle 116 with second face 108. For example, in one embodiment, angle 116 is about 30°. In another embodiment, angle 116 is between about 15° and about 45°. In some embodiments, first hole 110 and second hole 112 are positioned on a line 118, shown in FIG. 1, that bisects first aperture 102 and second aperture 104. A distance 120 (FIG. 5) is defined between central axis 111 of first hole 110 and an intersection of central axis 114 of second hole 112 with second face 108. As shown in FIGS. 4 and 5, in some embodiments, cut guide 100 includes a boss 122 extending from first face 106. In such embodiments, second hole 112 may extend through boss 122. Boss 122 may include a face 124 orthogonal to central axis 114.

In various embodiments, as shown in FIGS. 1, 3, and 5, cut guide 100 may include a window 126 extending through the cut guide 100 from first face 106 to second face 108. As described further herein, window 126 allows the wire positioned in second hole 112 to be viewed (e.g., directly or using fluoroscopy or other imaging modality) to ensure that the wire is properly aligned.

Cut guide 100 may be constructed of any appropriate material. For example, in some embodiments, cut guide 100 is constructed from stainless steel.

In another aspect, a targeting guide is provided to guide the insertion of wires into a bone for securing the bone after cutting of the bone (e.g., using cut guide 100 described above). FIGS. 8-14 show a targeting guide 200 according to one embodiment. As shown, for example, in FIG. 8, targeting guide 200 includes a coupling member 202 configured to couple to a wire and to a bone. Targeting guide 200 further includes an arm 204 extending from coupling member 202 and a targeting member 206 (shown in FIG. 9) extending from the opposite end of the arm 204.

Figure 11:
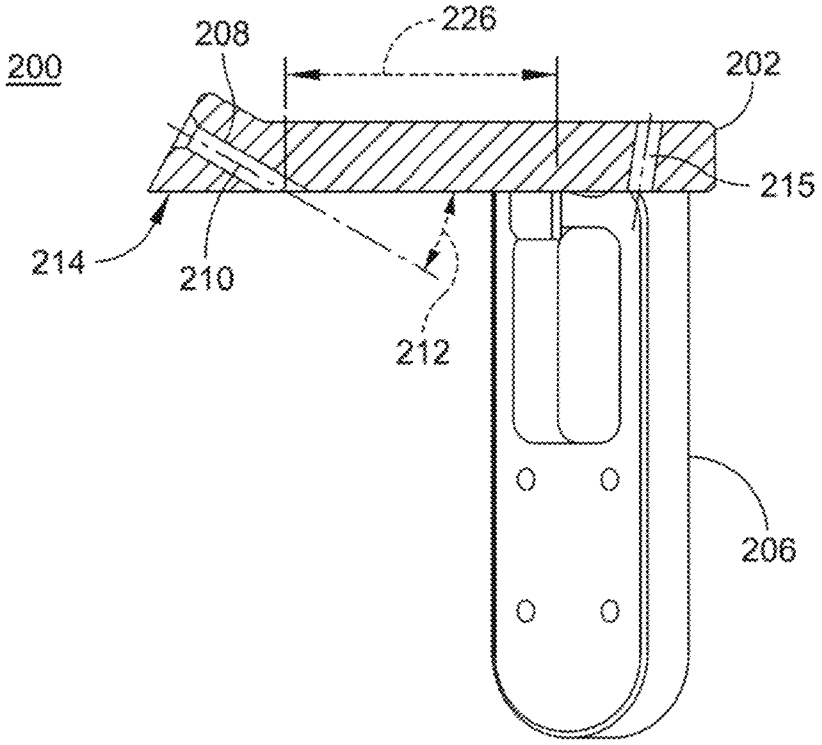
FIG. 11 is a cross-sectional view of the targeting guide of FIG. 8.

Coupling member 202 includes a coupling hole 208 configured to receive a wire. As shown in FIG. 11, coupling hole 208 defines a central axis 210 that forms an acute angle 212 with a bone facing surface 214 of coupling member 202.

As will be described further herein, this may allow targeting guide 200 to receive the wire used with cut guide 100 described above. In various embodiments, angle 212 is the same as angle 116 defined by central axis 114 of second hole 112 of cut guide 100. In one embodiment, angle 212 is about 30°. In one embodiment, angle 212 is between about 15° and about 45°.

Figure 10:
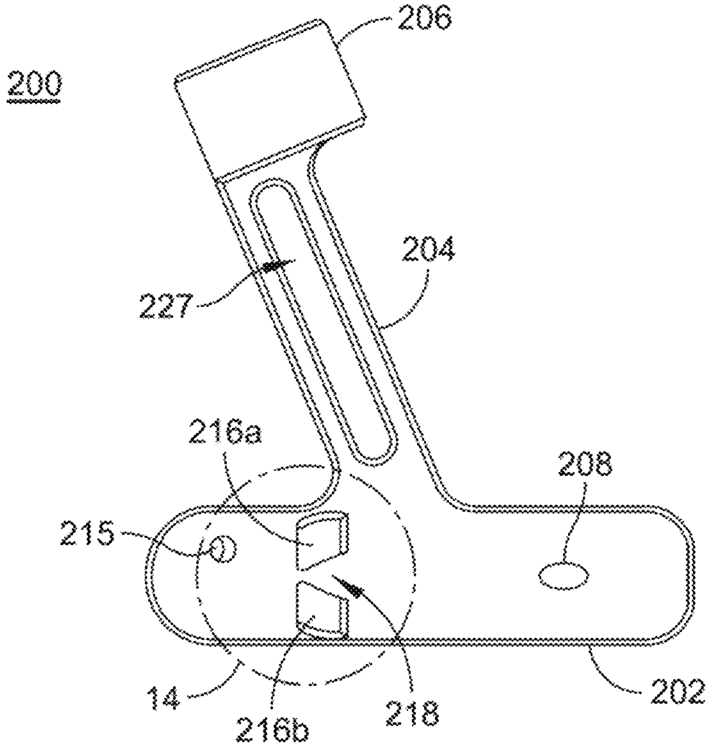

As shown in FIGS. 10 and 11, coupling member 202 may further include a distal hole 215. As will be described herein, a wire may be inserted through distal hole 215 and into a bone to secure targeting guide 200 in place. In some embodiments, distal hole 215 may form an acute angle with bone facing surface 214. Further, in some embodiments, distal hole 215 is vertically offset from coupling hole 208, as shown, for example, in FIG. 8. The angle and position of distal hole 215 may ensure that a wire inserted in distal hole 215 does not cross the cuts in the bone formed using cut guide 100.

Figure 9:
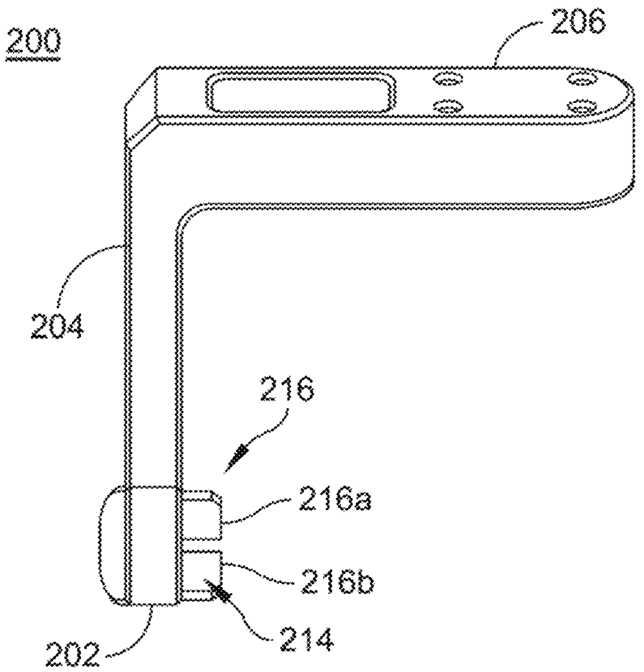
Figure 14:
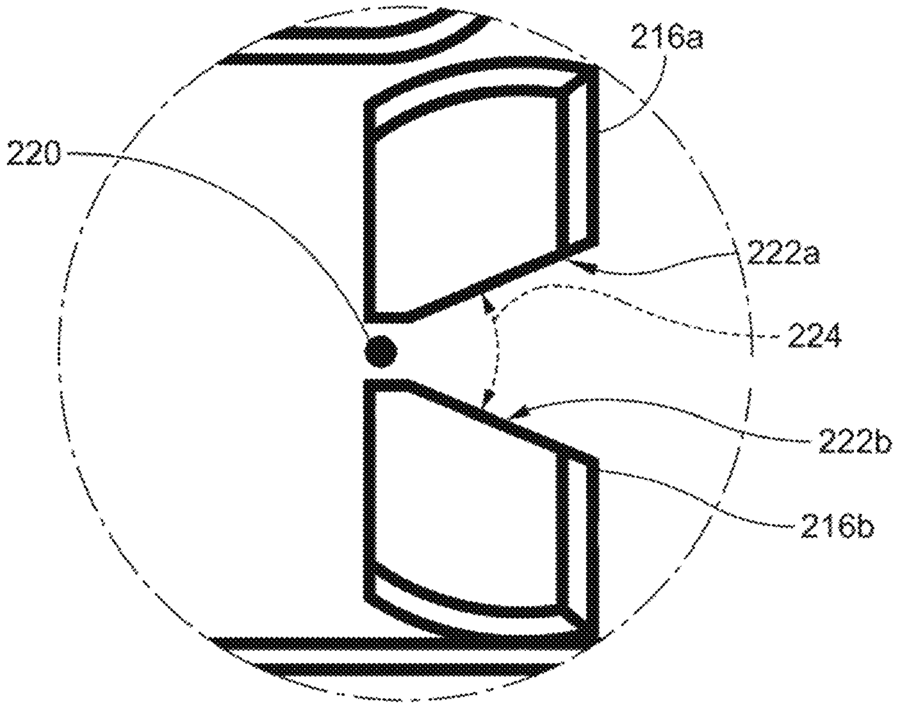
FIG. 14 is a detail view of projections of the targeting guide of FIG. 8.

Coupling member 202 may further include one or more projections 216 extending from bone facing surface 214. For example, as shown in FIGS. 9 and 10, a first projection 216*a* and a second projection 216*b* may extend from bone facing surface 214. As shown, for example, in FIG. 10, first 216*a* and second 216*b* projection form a v-shaped cavity 218 between the first 216*a* and second 216*b* projections. Cavity 218 has an apex 220 (FIG. 14). As described below, projections 216 are configured to receive and engage a bone that has been cut into a v- or chevron-shape (e.g., using cut guide 100 described above). As shown in FIG. 14, each projection 216 includes a mating face 222 and mating faces 222*a*, 222*b* are oriented such that they define an angle 224 between them. In various embodiments, angle 224 is about 45°. In addition, a distance 226 is defined between apex 220 and the intersection of central axis 210 and bone facing surface 214, as shown in FIG. 11. In various embodiments, distance 226 is approximately equal to distance 120 between first hole 110 and second hole 112 of cut guide 100. This may allow projections 216*a*, 216*b* to engage the end of the bone when engaged with a wire, as described herein. Although the illustrated embodiment includes two projections 216 forming cavity 218. In other embodiments, cavity 218 is formed by a single projection or any other number of projections.

Arm 204 may extend from coupling member 202 at an angle. For example, in one embodiment, arm 204 extends from coupling member 202 at an angle of about 68°. In another embodiment, arm 204 extends from coupling member 202 at an angle of between about 53° and about 83°. In various embodiments, arm 204 may further include a window 227 that allows a user to verify the position and orientation of fixation wires inserted using targeting guide 200, either directly or using fluoroscopy or other imaging modality. In some embodiments, the orientation of arm 204 is selected such that targeting member 206 is oriented parallel to a cut face of a bone (e.g., formed in conjunction with cut guide 100), as explained in more detail herein.

Targeting member 206 extends from arm 204 such that targeting member 206 is generally orthogonal to bone facing surface 214 of coupling member 202. Targeting member 206 includes one or more targeting holes 228 configured to guide the insertion of guide wires into a bone, as described herein. Targeting holes 228 are each oriented such that a wire inserted therein is positioned such that it intersects the approximate center of the bone.

Figure 12:
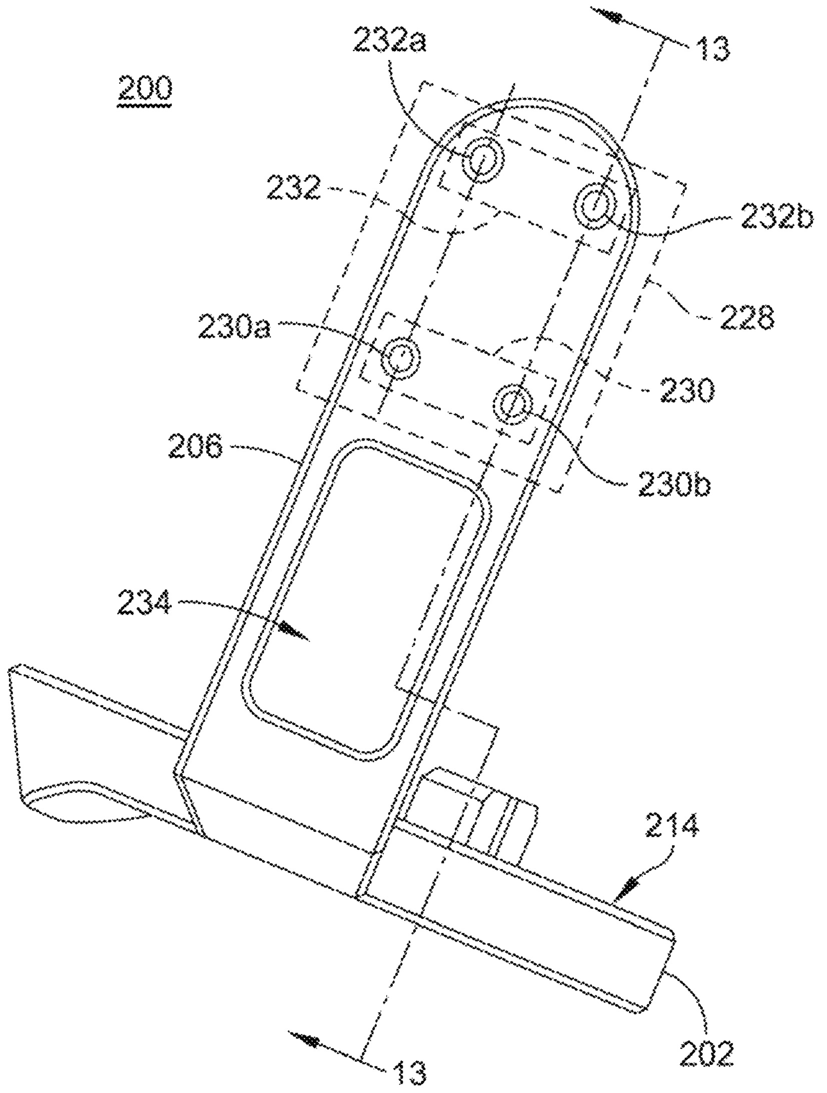
FIG. 12 is a top view of the targeting guide of FIG. 8.
Figure 13:
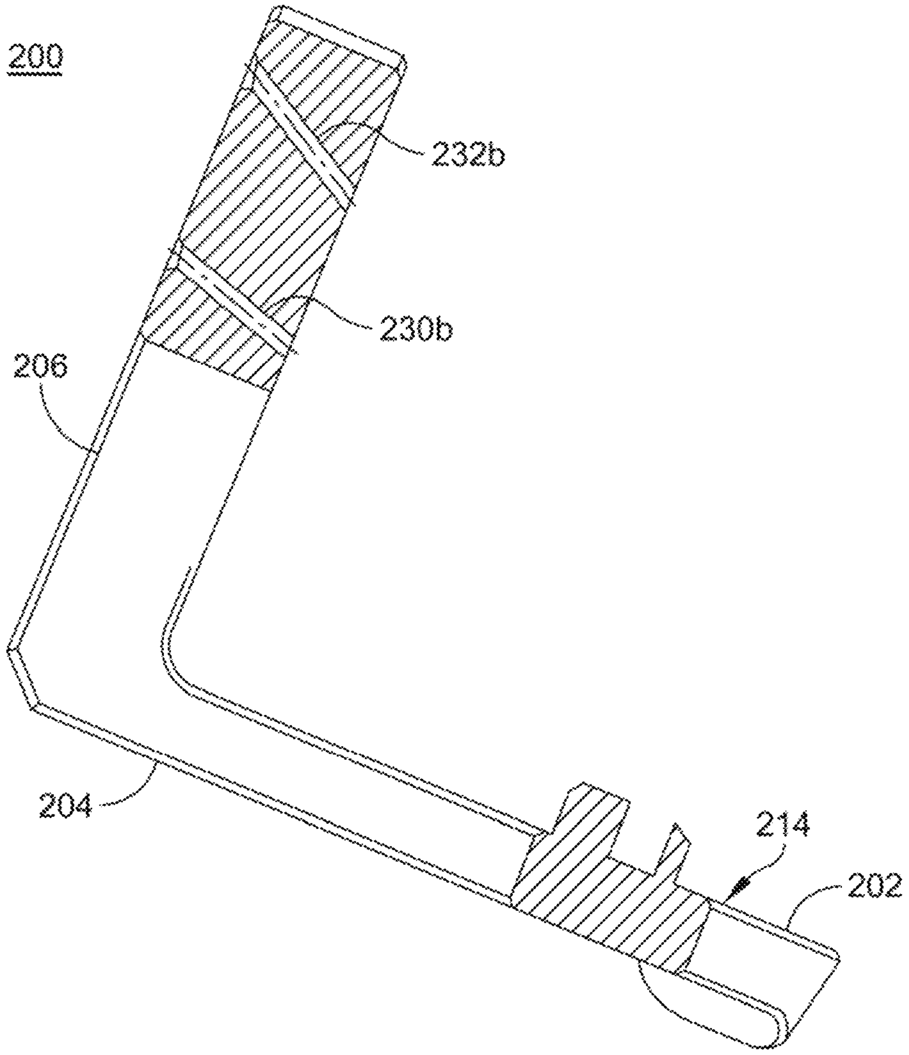
FIG. 13 is a cross-sectional view of the targeting guide of FIG. 8.

As shown best in FIG. 12, in various embodiments, targeting member 206 includes a first set 230 of targeting holes 228. In at least one embodiment, each hole 230*a*, 230*b* in the first set 230 of targeting holes 228 is equally spaced from bone facing surface 214. Further, in various embodiments, the central axes of the holes 230*a*, 230*b* in the first set of holes 230 are parallel to one another, as shown in FIG. 13.

In various embodiments, targeting member 206 may further include a second set 232 of targeting holes 228. As shown in FIG. 12, the second set of holes 232 is offset from the first set 230 in a direction orthogonal to bone facing surface 214. In various embodiments, the central axes of the holes 232*a*, 232*b* of second set of holes 232 are parallel to one another, as shown in FIG. 13. As shown in FIG. 13, in various embodiments, the holes 232*a*, 232*b* of the second set of holes 232 are not parallel to the holes of the first set of holes 230. This may allow a user to choose between first set 230 of targeting holes 228 and second set 232 of targeting holes 228 when performing a procedure, as described herein. The holes 232*a*, 232*b* of the second set of holes 232 are oriented at a steeper angle with respect to the bone facing surface 214 than those of the first set of holes 230. However, they may still be configured to target the center of the bone. For example, each hole of the first set of holes 230 may be oriented at an angle of about 17° with respect to bone facing surface 214 and each hole of the second set of holes 232 may be oriented at an angle of about 30° with respect to bone facing surface 214.

In some embodiments, targeting member 206 further includes a window 234 that can be used by a user to view the position and orientation of fixation wires inserted using targeting guide 200 (either directly or using fluoroscopy or other imaging modality).

As shown in FIGS. 8-13, targeting guide 200 may be a single, unitary piece. For example, coupling member 202, arm 204, and targeting member 206 may be integrally formed (e.g., machined from a single piece of material, cast, injection molded, or formed through additive manufacturing). Alternatively, one or more of coupling member 202, arm 204, and targeting member 206 may be joined by welding or other method. Targeting guide 200 may be constructed of any appropriate material. For example, in various embodiments, targeting guide 200 is constructed from a metallic alloy, such as an alloy containing Titanium.

Figure 15B:
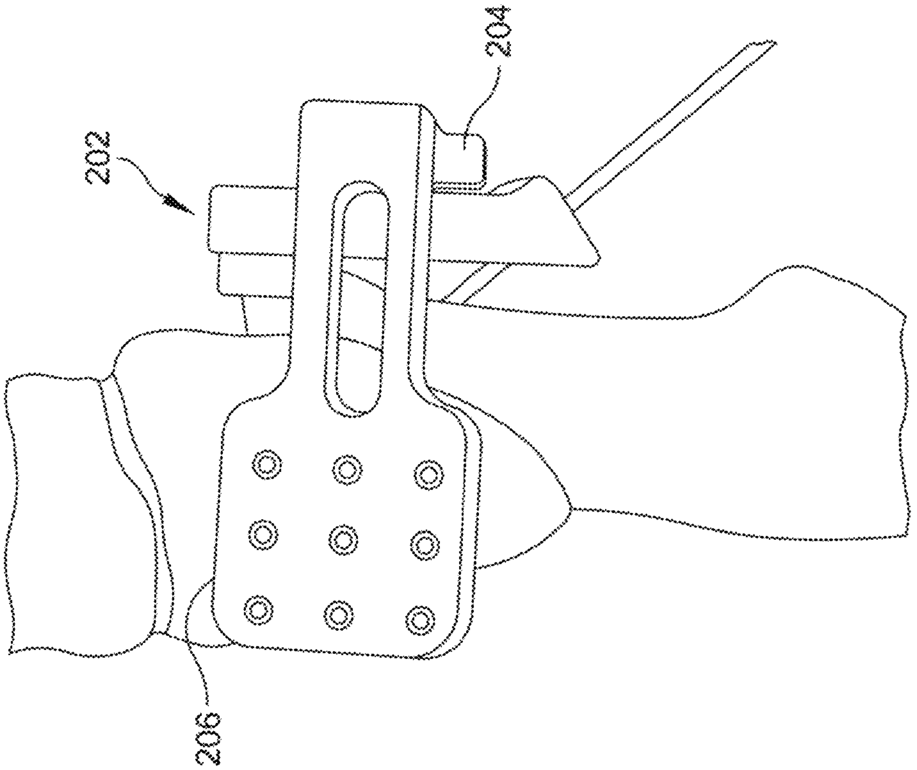
FIGS. 15A and 15B are top views of a targeting guide, according to another embodiment described herein in use.
Figure 15A:
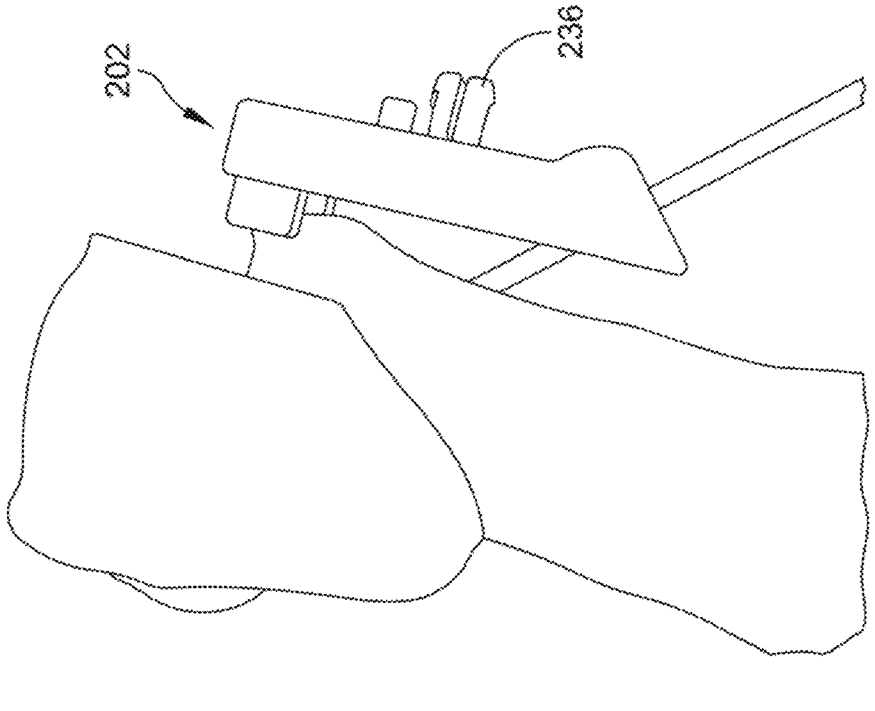

In other embodiments, shown in FIGS. 15A and 15B, targeting guide 200 is constructed from more than one piece. For example, coupling member 202 may be separate from arm 204 and targeting member 206. In such embodiments, the separate components may be joined before or during a procedure. For example, in one embodiment, coupling member 202 includes flex arms 236 configured to engage arm 204, for example, after engaging coupling member 202 with a bone.

Figure 16:
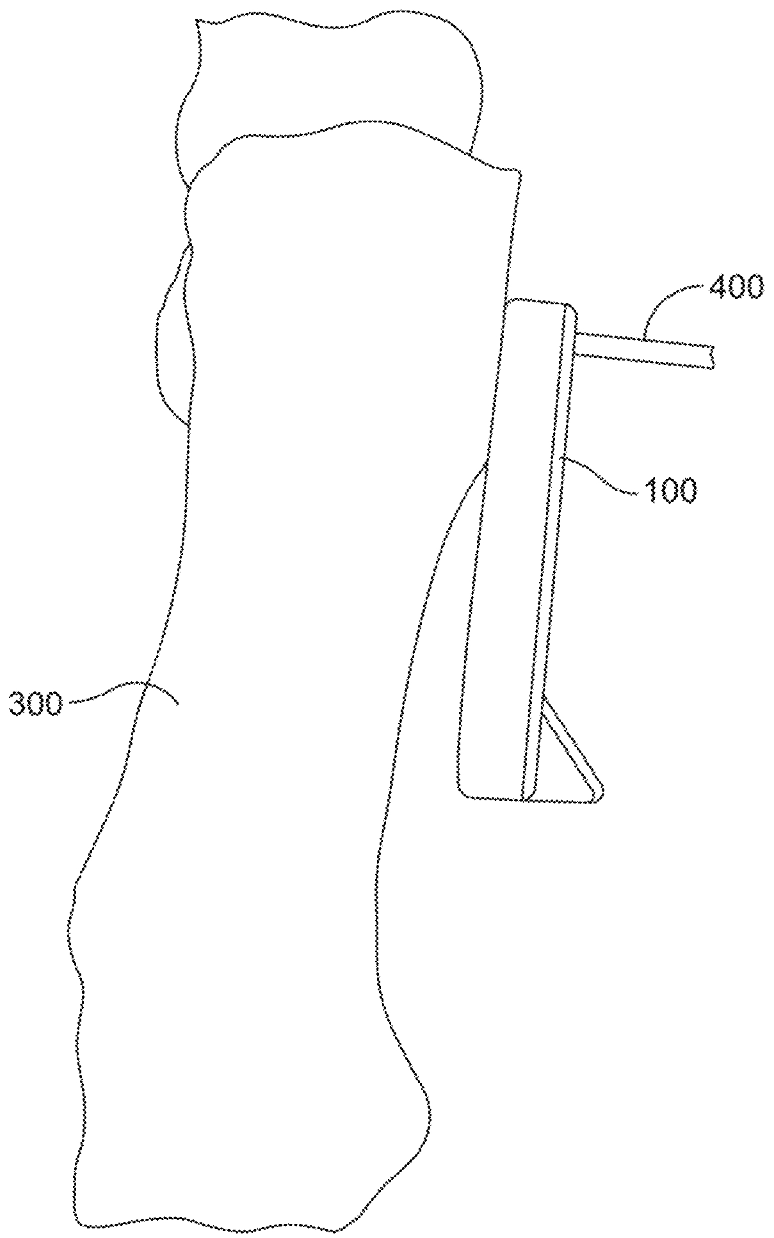
FIG. 16 is a top view of a cut guide in place against a prepared surface of a metatarsal.
Figure 17:
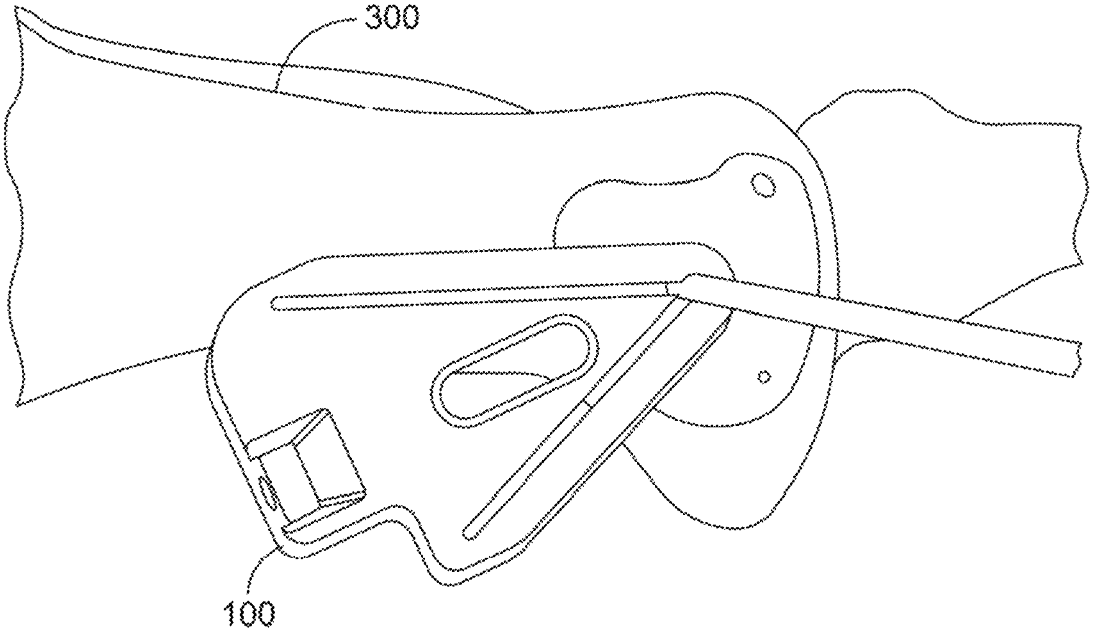
FIG. 17 is a medial view of the cut guide being positioned against the cut surface of the metatarsal.
Figure 18:
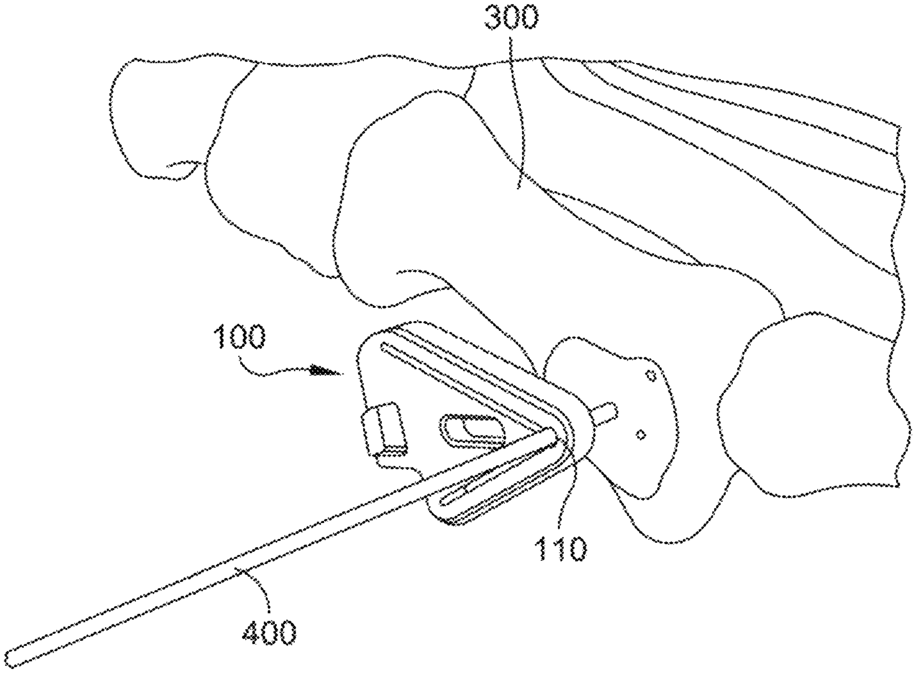
FIG. 18 is a perspective view of the cut guide being positioned against the cut surface of the metatarsal.

Turning to FIGS. 16-30, a method for reducing a patient's hallux valgus angle using a cut guide (e.g., cut guide 100) and a targeting guide (e.g., targeting guide 200) is illustrated. In various embodiments, the first metatarsal 300 is first prepared by removing the medial eminence of first metatarsal 300 using a surgical saw or other cutting instrument. Such a prepared first metatarsal 300 is shown in FIGS. 16-18. In some embodiments, a guide is provided for use in preparing the metatarsal. After preparation of first metatarsal 300, a first wire 400 is inserted into the apex of the metatarsal head. In various embodiments, first wire 400 is inserted orthogonal to the planar face prepared using the cutting instrument, as shown, for example, in FIG. 16.

As shown in FIGS. 16-18, first hole 110 in cut guide 100 is slid over first wire 400 and cut guide 100 is positioned proximate first metatarsal 300. Alternatively, in some embodiments, cut guide 100 is used as a guide for insertion of first wire 400. In some embodiments, as shown in FIGS.

Figure 19:
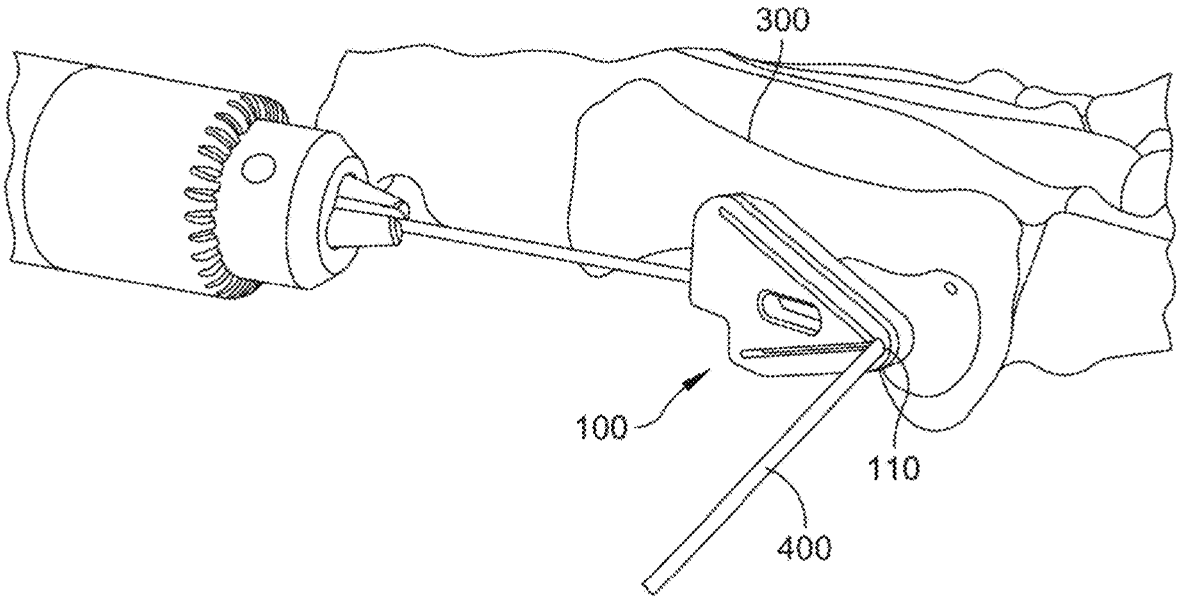
FIG. 19 is a perspective medial view of a second wire being inserted through a hole in the cut guide and into the metatarsal.
Figure 20:
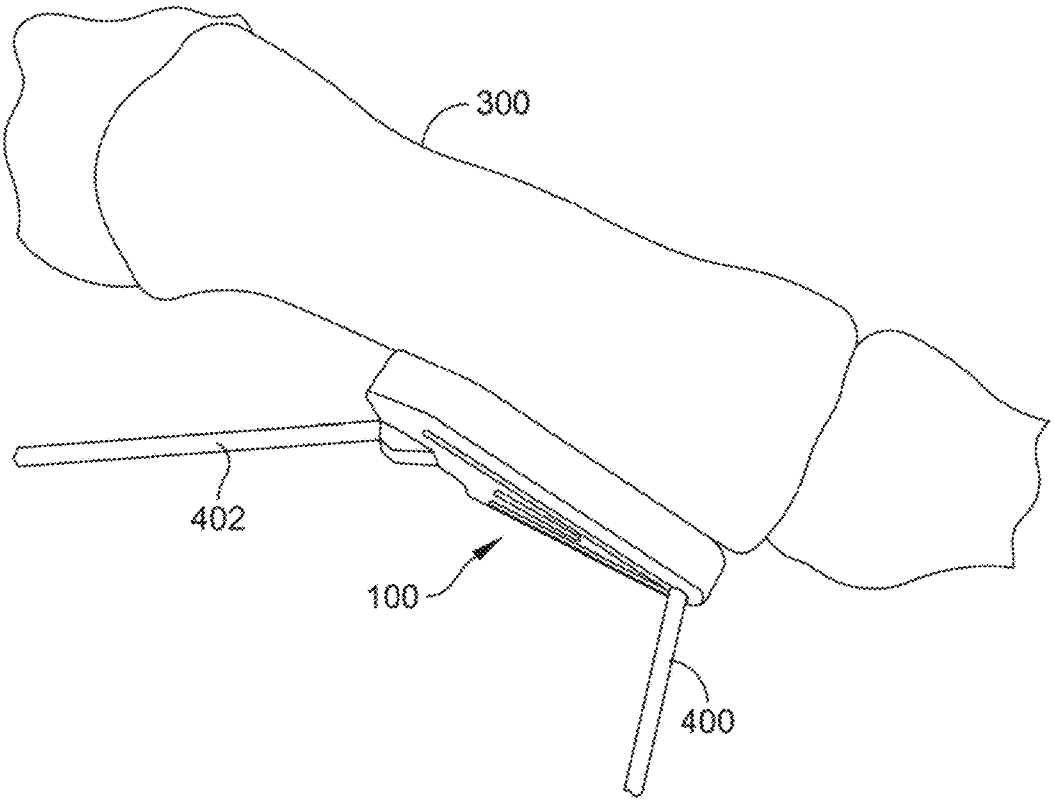
FIG. 20 is a perspective view of the cut guide fixed in position against the metatarsal.
Figure 20B:
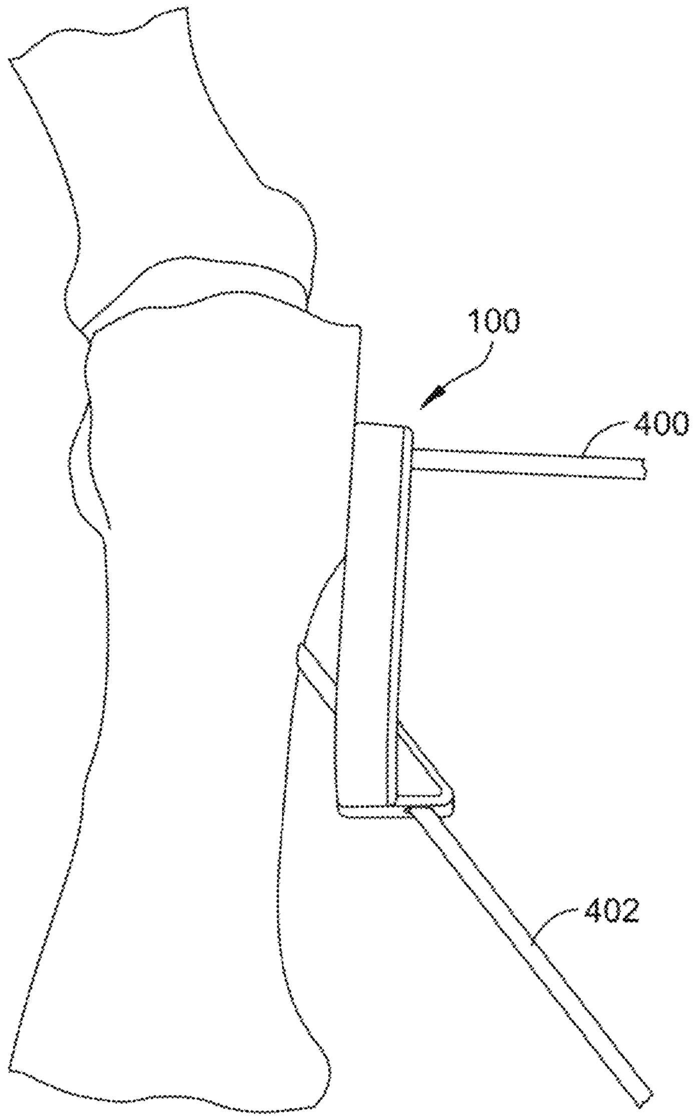
FIG. 20B is a top view of the cut guide fixed in position against the metatarsal.

16 and 20B, second face 108 is placed against the prepared face of first metatarsal 300. With cut guide 100 in contact with first metatarsal 300, a second hole is formed in the first metatarsal 300. For example, as shown in FIGS. 19 and 20, a second wire 402 is inserted through second hole 112 and into first metatarsal 300 (e.g., using a drill). Because second wire 402 is at an angle with respect to first wire 400, cut guide 100 is fixed in position. This eliminates the need for additional wires or other components to secure the cut guide in place. In some embodiments, the depth of insertion of second wire 402 is controlled. For example, second wire 402 may include a laser mark, groove, color identifier, change in finish, or other identifying mark. The user may insert second wire 402 until the identifying mark is approximately aligned with face 124 of cut guide 100. In some embodiments, the depth of insertion of second wire 402 is limited such that second wire 402 does not extend beyond the osteotomy cut described below. During and/or after insertion of second wire 402, the user can visualize the alignment and placement of second wire 402 using window 126. The placement and orientation of second wire 402 may be viewed directly or, alternatively, using fluoroscopy or other imaging modalities. In some embodiments, second wire 402 is aligned with the longitudinal axis of first metatarsal 300 when viewed in the lateral to medial direction.

Figure 21:
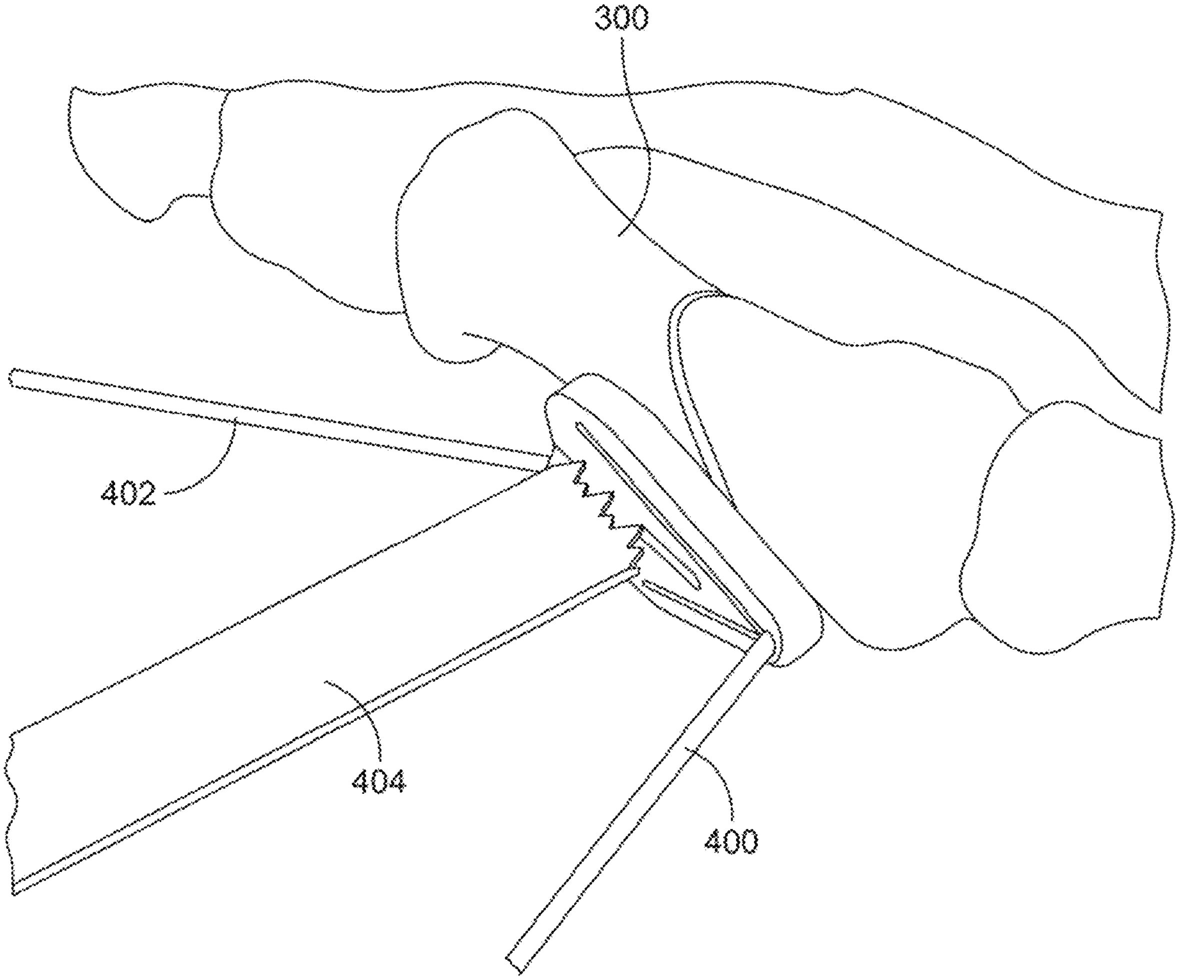
FIG. 21 shows the use of a cutting instrument and the cut guide to form a cut in the metatarsal.

With cut guide 100 fixed in position, a surgical tool 404, such as a surgical saw, is used to cut first metatarsal 300, as shown in FIG. 21. Surgical tool 404 may be guided by first aperture 102 and second aperture 104 of cut guide 100 to form a chevron-shaped cut in first metatarsal 300, thereby separating a first bone portion 302 from a second bone portion 304.

Figure 22:
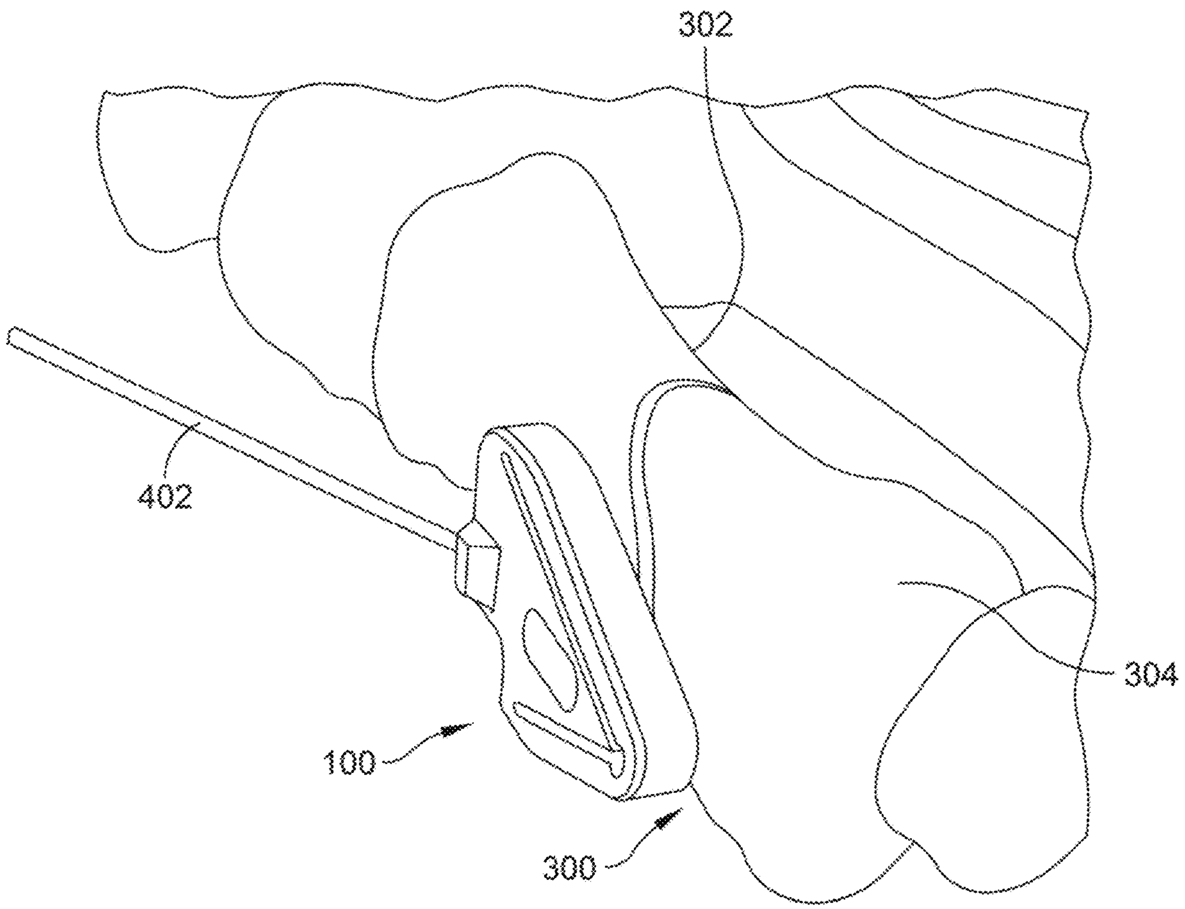
FIG. 22 is a perspective view after removal of the first wire from the metatarsal and cut guide.
Figure 23:
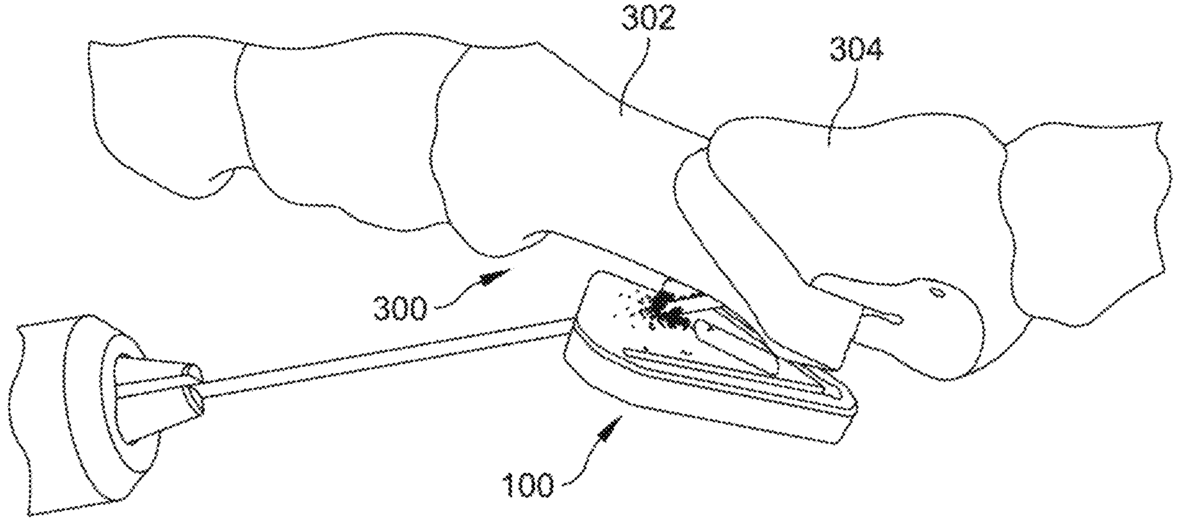
FIG. 23 shows insertion of the second wire deeper into the metatarsal after repositioning of the bone portions.
Figure 24:
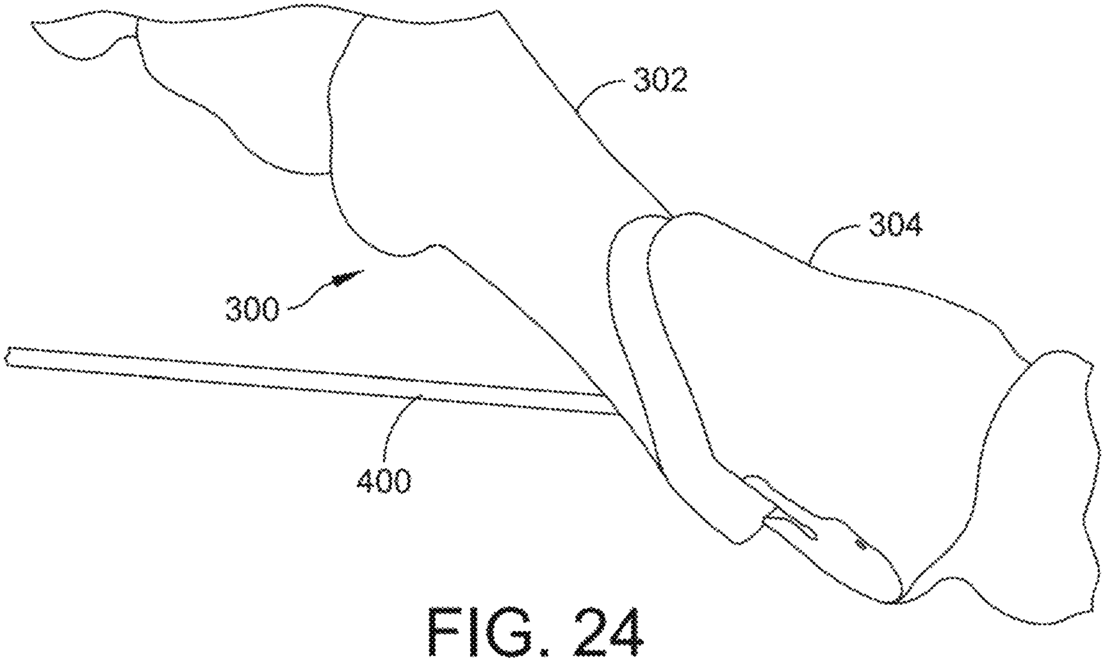
FIG. 24 is a perspective view of the metatarsal after removal of the cut guide.

After completion of the cut, first wire 400 may be removed, as shown in FIG. 22. Cut guide 100 can then be removed by sliding it off of second wire 402. The first 302 and second 304 bone portions are then shifted to the desired position. As shown in FIG. 23, second wire 402 may be inserted deeper into metatarsal 300 such that it spans first 302 and second 304 bone portions either before or after removal of the cut guide 100. This temporarily fixes the relative positions of first 302 and second 304 bone portions. In other embodiments, second wire 402 is removed from metatarsal 300 and subsequently reinserted, as described below.

Figure 25:
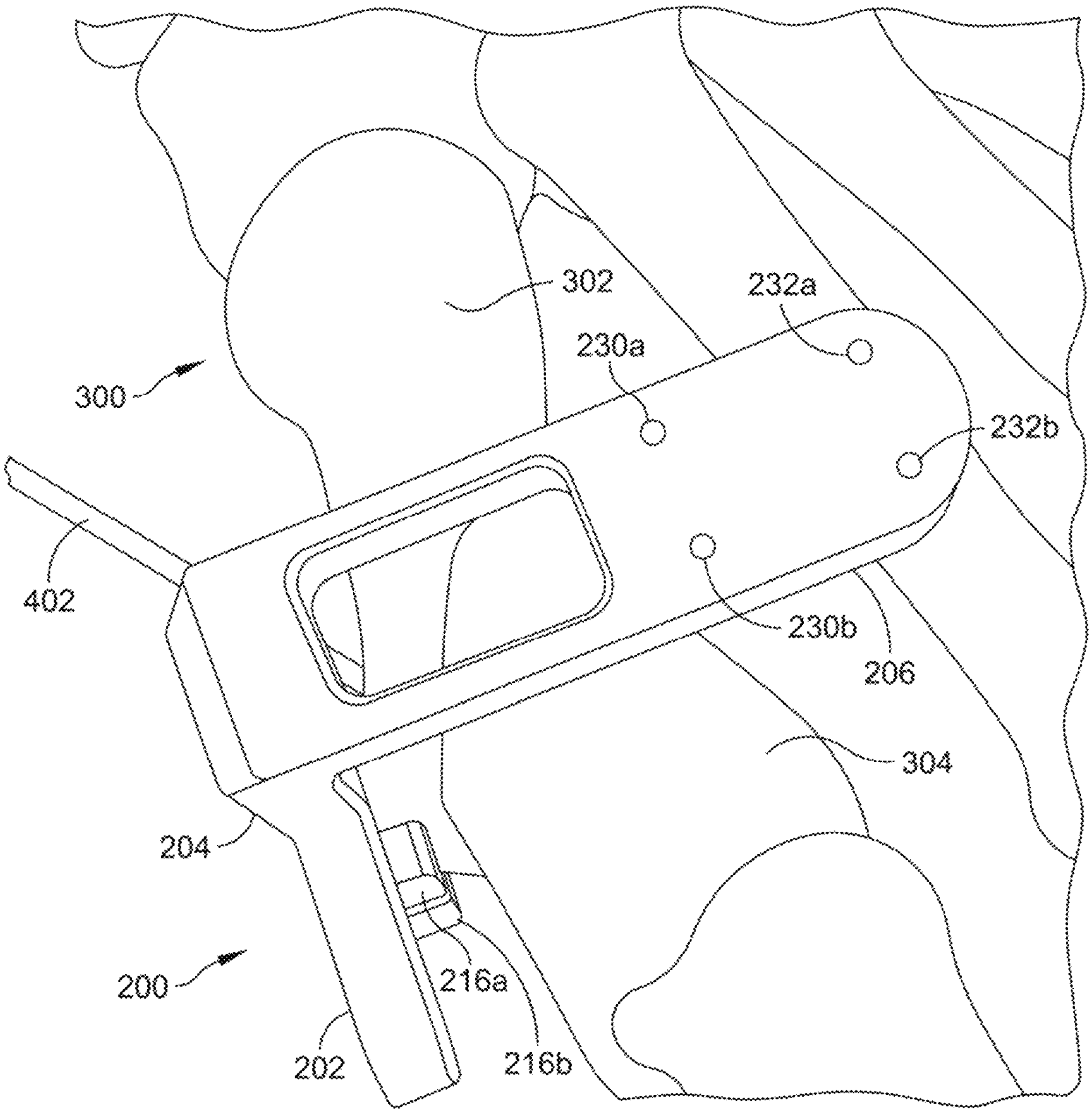
FIG. 25 is a perspective view of a targeting guide in place on the metatarsal.
Figure 26:
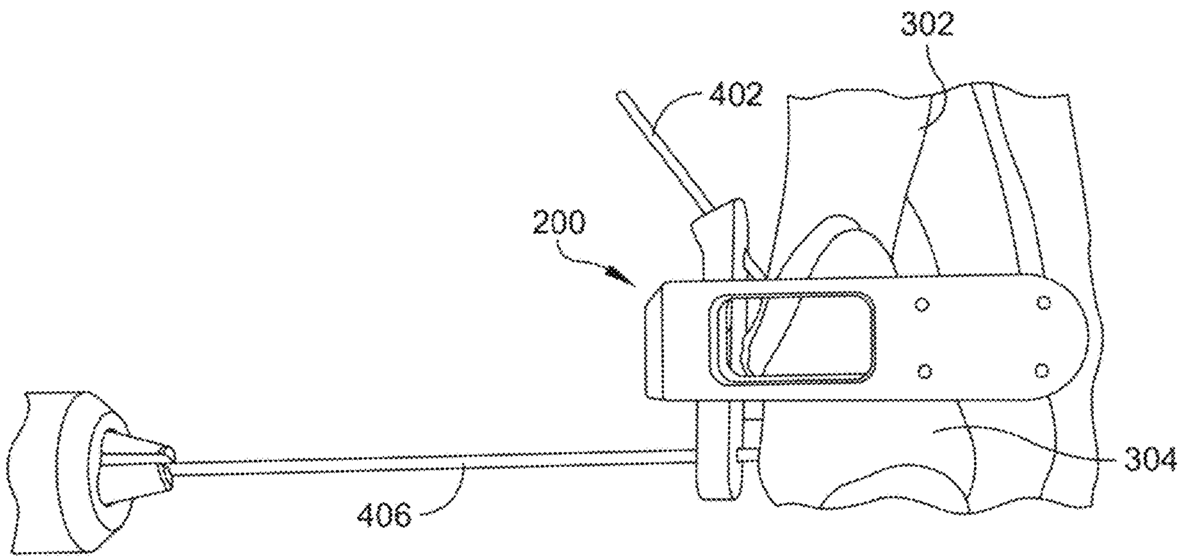
FIG. 26 is a perspective view showing insertion of an additional wire through the targeting guide and into the metatarsal.
Figure 27:
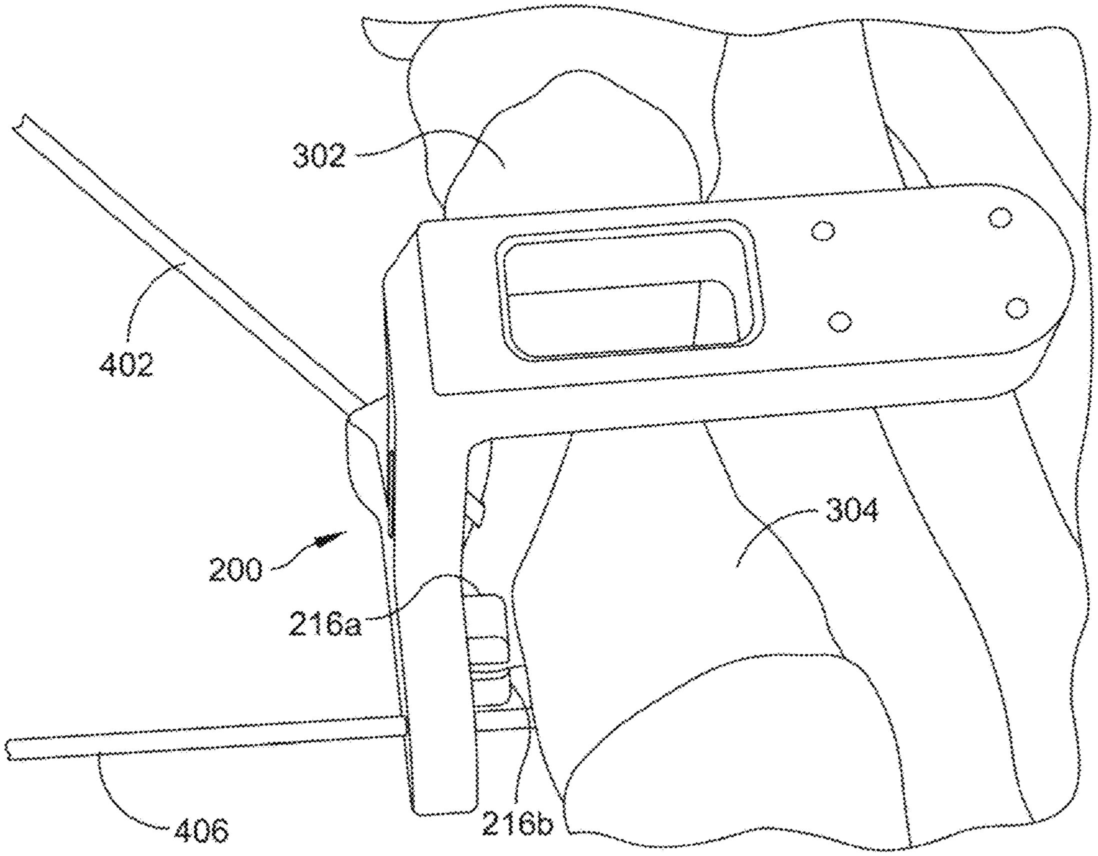
FIG. 27 is a perspective view after insertion of the additional wire through the targeting guide and into the metatarsal.

As shown in FIG. 25, in embodiments in which second wire 402 remains in place, targeting guide 200 is moved toward metatarsal 300 such that second wire 402 passes through coupling hole 208. In addition, cavity 218 formed by projections 216 is engaged with the v-shaped end of first bone portion 302 formed using surgical tool 404 and cut guide 100, as described above. This engagement retains targeting guide 200 in position. In some embodiments, as projections 216 are brought into engagement with the end of first bone portion 302, second wire 402 is flexed or bent. As a result, when projections 216 are engaged with first bone portion 302, second wire 402 applies an elastic biasing force on targeting guide 200 to lock it in place. Optionally, an additional wire 406 can be inserted through distal hole 215 of targeting guide 200 and into second bone portion 304, as shown in FIGS. 26 and 27, to further secure targeting guide 200 in position.

In embodiments in which second wire 402 is removed prior to placement of targeting guide 200, projections 216 may first be engaged with first bone portion 302. Second wire 402 is subsequently reinserted by passing it through coupling hole 208 and into metatarsal 300.

Figure 30:
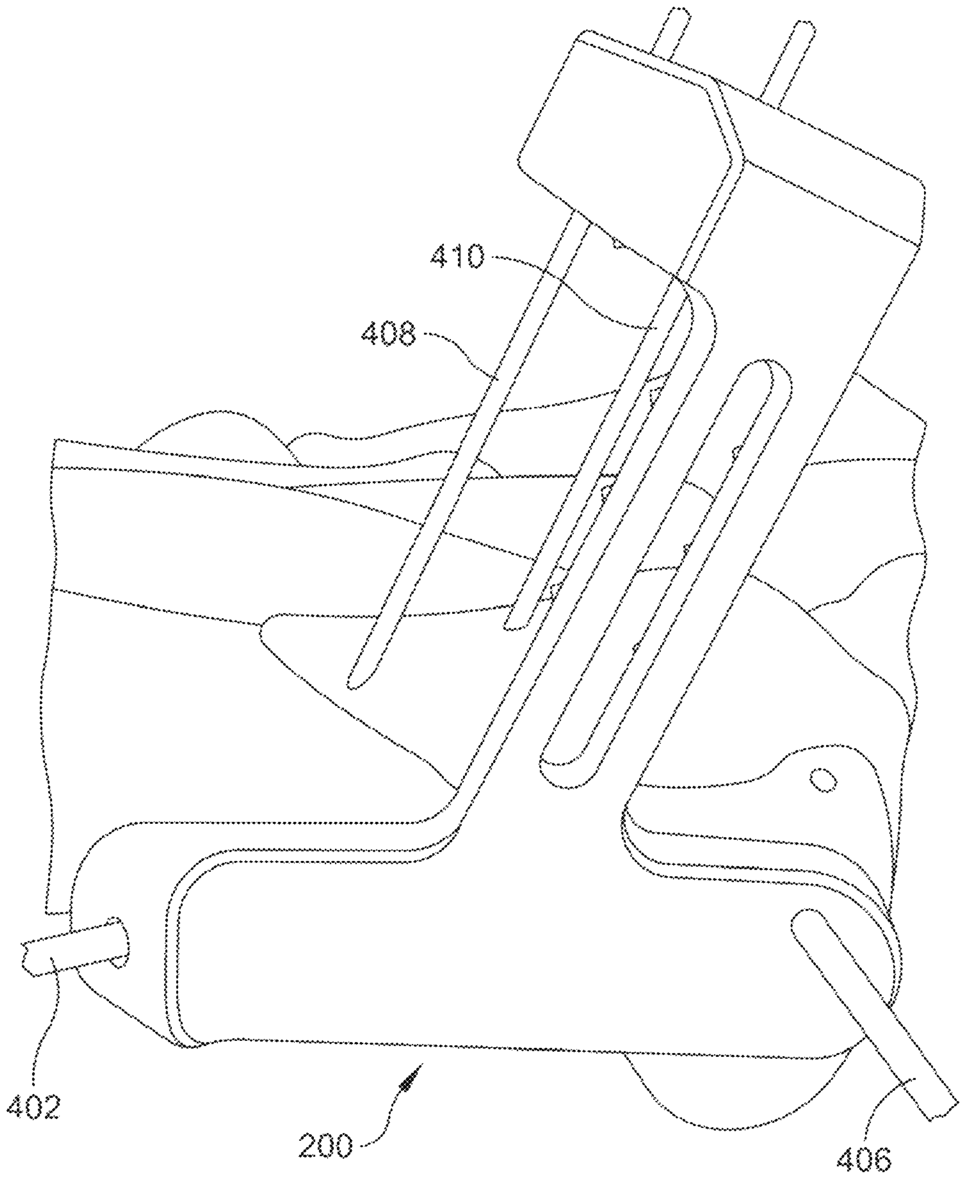
FIG. 30 is a medial view after insertion of the second fixation wire through the targeting guide and into the metatarsal.

As shown best in FIG. 30, when targeting guide 200 is positioned using second wire 402 and projections 216, targeting member 206 is approximately parallel to the top cut surface of first bone portion 302 (i.e., the surface formed by inserting a cutting instrument through first aperture 102 of cut guide 100). This allows targeting wires to be inserted through first and second bone portions 302, 304 at a desired orientation.

Figure 28:
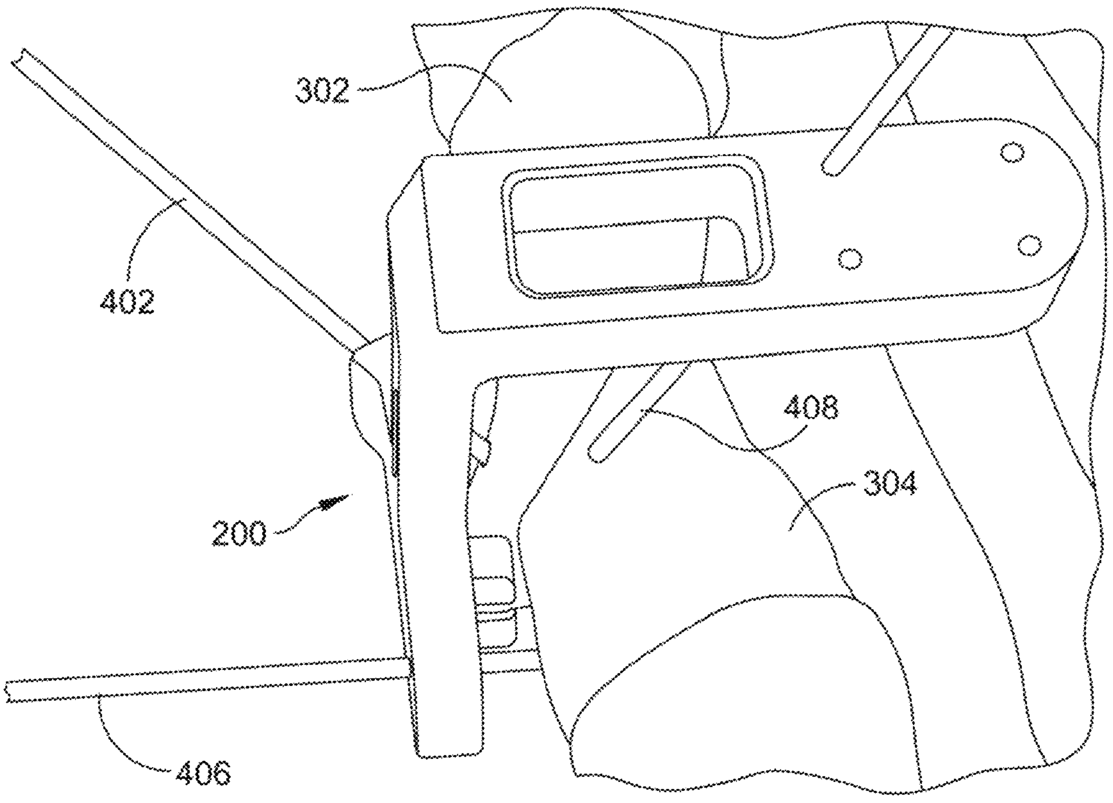
FIG. 28 is a perspective view after insertion of a first fixation wire through the targeting guide and into the metatarsal.
Figure 29:
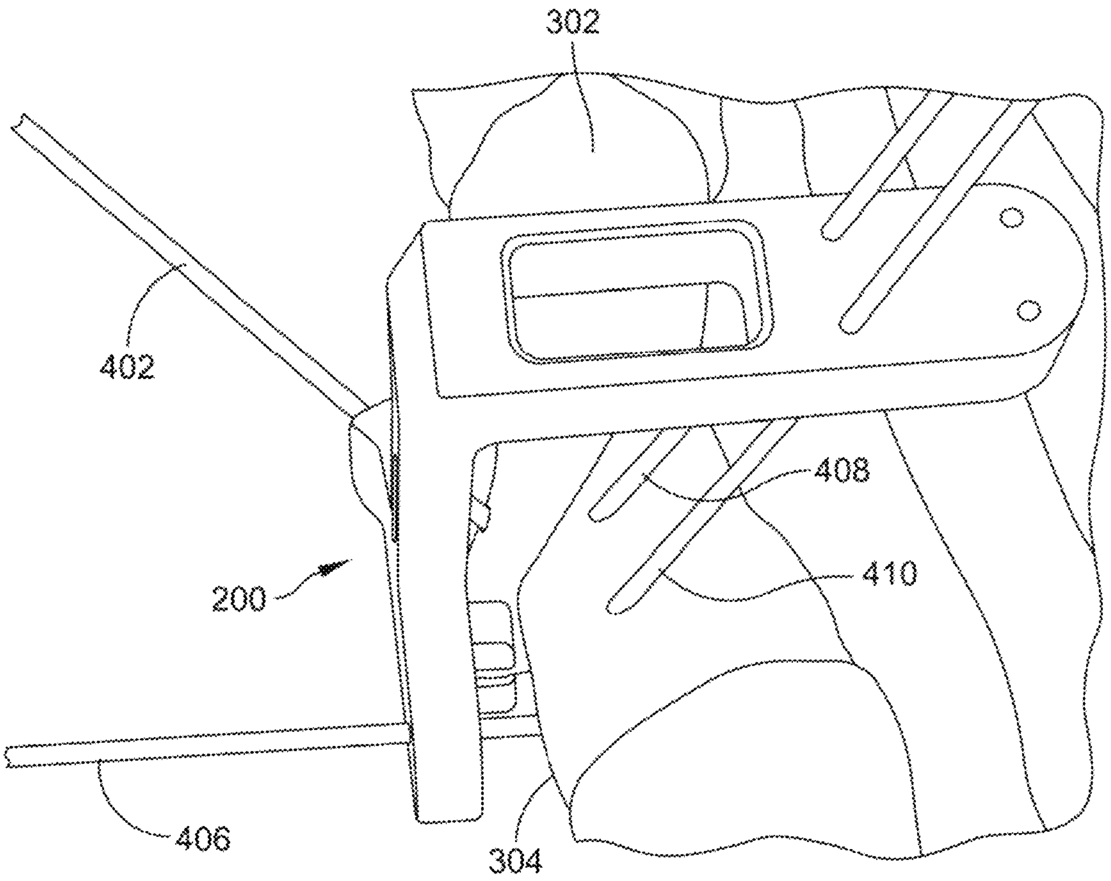
FIG. 29 is a perspective view after insertion of a second fixation wire through the targeting guide and into the metatarsal.

The user selects a set of targeting holes (e.g., first set 230 or second set 232) through which to insert wires for guiding the insertion of fixation screws through first bone portion 302 and second bone portion 304. The respective sets of targeting holes have different angles of approach to the bone, thereby allowing the user to select the appropriate angle based on the patient's anatomy. The user then inserts a first fixation wire 408 through a first of the selected set of targeting holes, as shown in FIG. 28. The user then inserts a second fixation wire 410 into the second of the set of targeting holes, as shown in FIGS. 29 and 30. As described above, the targeting holes orient the first fixation wire 408 and the second fixation wire 410 such that they are approximately parallel to one another. The fixation wires 408, 410 extend through the first 302 and second 304 bone portions to temporarily fix them in position with respect to one another.

After placement of the fixation wires 408, 410, second wire 402 can be removed from first and second bone portions 302, 304 and targeting guide 200 can be removed by sliding it off of fixation wires 408, 410. If a distal wire 306 is used to secure targeting guide 200, it can be removed before sliding targeting guide 200 off of fixation wires 408, 410.

After removal, first and second bone portions 302, 304 can be secured in place using bone screws. For example, cannulated screws can be inserted into first and second bone portions 302, 304 by passing the screws over fixation wires 408, 410. With the screws in place, fixation wires 408, 410 can be removed from first and second bone portions 302, 304.

In various embodiments, the cut guides and targeting guides described herein may be provided in a kit. Further, the cut guides and targeting guides described herein may be provided in both a left and right configuration (i.e., configured to be used on the left and right foot, respectively). Such right and left configurations can be supplied in separate kits or, alternatively, in a single kit. In some embodiments, the cut guides and targeting guides may include features that allow the left and right configurations to be easily identified. For example, the guides may be identified with a "Left" or "L" marking. Additionally, or alternatively, the geometry of the right and left configurations may differ. For example, as shown in FIG. 1, cut guide 100 may include a cutout 128 that makes it easy to determine the proper orientation of cut guide 100.

While the foregoing description and drawings represent preferred or exemplary embodiments of the present invention, it will be understood that various additions, modifications and substitutions may be made therein without departing from the spirit and scope and range of equivalents of the accompanying claims. In particular, it will be clear to those skilled in the art that the present invention may be embodied in other forms, structures, arrangements, proportions, sizes, and with other elements, materials, and components, without departing from the spirit or essential characteristics thereof. One skilled in the art will further appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims and equivalents thereof, and not limited to the foregoing description or embodiments. Rather, the appended claims should be construed broadly, to include other variants and embodiments of the invention, which may be made by those skilled in the art without departing from the scope and range of equivalents of the invention. All patents and published patent applications identified herein are incorporated herein by reference in their entireties.

The invention claimed is:

1. A method comprising:

inserting a first wire into a bone;

providing a cut guide including a first elongate aperture and a second elongate aperture communicating between a first face and a second face and arranged so as to define an intersection at an acute angle, a first hole located at the intersection communicating between the first face and the second face, a second hole defined through the cut guide, wherein a central axis of the second hole is oriented at an acute angle in the range from 15° to 45° relative to the second face, wherein the first and second holes are each sized to receive a wire and configured so as to position the cut guide against the bone;

sliding the cut guide over the first wire such that the first wire is disposed within the first hole;

inserting a second wire through the second hole such that first wire and the second wire define an acute angle;

inserting a surgical tool through at least one of the first elongate aperture and the second elongate aperture so as to be positioned and configured to cut and separate the bone into a first bone portion and a second bone portion; and increasing a depth of insertion of the second wire such that the second wire engages both the first bone portion and the second bone portion to prevent relative movement of the first and second bone portions.

2. The method of claim 1, further comprising removing the first wire from the bone and sliding the cut guide off of the second wire.

3. The method of claim 2, further comprising:

repositioning the second bone portion with respect to the first bone portion before the increasing of the depth of insertion of the second wire.

4. The method of claim 1, further comprising sliding a targeting guide over the second wire and engaging the targeting guide with the first bone portion.

5. The method of claim 4, wherein, after the targeting guide is slid over the second wire, flexing the second wire as first and second projections located on the targeting guide are brought into engagement with the first bone portion thereby creating an elastic biasing force that locks the targeting guide in position relative to the bone.

6. The method of claim 5, further comprising inserting an additional wire into a distal hole defined through the targeting guide and into the second bone portion to augment fixation of the targeting guide during placement of fixation wires.

7. The method of claim 4, further comprising selecting, based on patient anatomy, one of;

(i) a first set of targeting holes that define a first acute angle relative to a bone-facing surface of the targeting guide, and (ii) a second set of targeting holes that define a steeper acute angle relative to the bone-facing surface of the targeting guide, and inserting first and second fixation wires through the selected set of targeting holes such that the fixation wires are substantially parallel to one another.

8. The method of claim 7, further comprising, after removal of the targeting guide, advancing first and second cannulated bone screws over the respective first and second fixation wires and into the first and second bone portions to secure the first and second bone portions in a corrective position, and thereafter removing the fixation wires.

9. The method of claim 1, further comprising limiting the depth of insertion of the second wire by advancing the second wire until a visual depth indicator provided on the second wire is substantially flush with a face of a boss located on the first face of the cut guide that is orthogonal to the central axis of the second hole.

10. The method of claim 9, further comprising verifying an orientation of the second wire through a window formed in the cut guide, the verifying step being performed by at least one of; (i) direct visual inspection and (ii) fluoroscopic imaging while the cut guide remains fixed to the bone.

11. A method comprising:

(a) preparing an osteotomy site on a metatarsal bone to expose a planar cut surface;

(b) inserting a coupling wire into the metatarsal bone at an acute angle relative to the planar cut surface;

(c) sliding a targeting guide over the coupling wire such that the coupling wire passes through a coupling hole of a coupling member of the targeting guide;

(d) engaging at least one projection extending from a bone-facing surface of the coupling member with a v-shaped end of a bone portion of the metatarsal bone;

(e) inserting an auxiliary wire through a distal hole of the coupling member and into the metatarsal bone to further stabilize the targeting guide;

(f) selecting a set of targeting holes provided in a targeting member of the targeting guide, the selected set defining a predetermined trajectory toward a central region of the metatarsal bone;

(g) inserting first and second fixation wires through respective targeting holes of the selected set and into the metatarsal bone along substantially parallel trajectories;

(h) removing the targeting guide while leaving the first and second fixation wires in place;

(i) advancing first and second cannulated bone screws over the respective first and second fixation wires and into the metatarsal bone to achieve fixation; and (j) removing the first and second fixation wires after the bone screws have been fully seated, wherein the targeting guide includes an arm having a viewing window, and the method further comprises visually confirming, through the viewing window, seating of the at least one projection and alignment of the first and second fixation wires prior to step (h).

12. A method, comprising:

inserting a first targeting wire into a bone;

providing a targeting guide including a coupling member defining a coupling hole extending through the coupling member, wherein the coupling hole is configured to receive the first targeting wire, a first projection extending from a bone facing surface of the coupling member, the first projection is configured to engage the bone, an arm extending from the coupling member and a targeting member coupled to the arm, the targeting member including at least one targeting hole for receiving and aligning a first fixation wire inserted into the bone;

sliding the targeting guide over the first targeting wire such that the first targeting wire is disposed through the coupling hole;

engaging the first projection extending from the bone facing surface with the bone;

inserting the first fixation wire through a first targeting hole of the at least one targeting hole;

inserting a second fixation wire through a second targeting hole of the at least one targeting hole, wherein the first and second targeting holes are equally spaced from the bone facing surface;

inserting a first screw into the bone along a trajectory defined by the first fixation wire; and inserting a second screw into the bone along a trajectory defined by the second fixation wire.

13. The method of claim 12, further comprising selecting, based on patient anatomy, one of a first set of targeting holes of the at least one targeting hole that define a first acute angle relative to the bone facing surface of the coupling member, and a second set of targeting holes of the at least one targeting hole that define a steeper acute angle relative to the bone facing surface of the coupling member, and the first and second targeting holes are in the selected set of targeting holes.

14. The method of claim 12, wherein the targeting member includes a window arranged for visually confirming a position and orientation of the first and second fixation wires during insertion.

15. The method of claim 12, further comprising inserting an additional wire through a distal hole of the coupling member and into the bone to further secure the targeting guide in position during placement of the first and second fixation wires.

16. The method of claim 12, wherein the first projection and a second projection project from the bone facing surface of the coupling member to form a v-shaped cavity, and the method further comprises engaging the v-shaped cavity with a complementary v-shaped surface of the bone.

17. The method of claim 12, wherein the first and second targeting holes are parallel to one another.

18. The method of claim 12, further comprising, after the inserting of the first and second fixation wires, removing the targeting guide, where the first and second screws are first and second cannulated bone screws which are advanced over the respective first and second fixation wires and into the bone, and thereafter removing the fixation wires.

19. The method of claim 12, wherein the coupling hole of the coupling member is oriented at an acute angle in the range from 15° to 45° relative to the bone facing surface of the coupling member.

* * * * *